United States Patent
Lau et al.

(10) Patent No.: US 6,670,142 B2
(45) Date of Patent: Dec. 30, 2003

(54) METHOD FOR SCREENING COMBINATORIAL BEAD LIBRARY, CAPTURING CELLS FROM BODY FLUIDS, AND LIGANDS FOR CANCER CELLS

(75) Inventors: Derick H. Lau, Gold River, CA (US); Kit S. Lam, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/032,678

(22) Filed: Oct. 26, 2001

(65) Prior Publication Data

US 2003/0170735 A1 Sep. 11, 2003

(51) Int. Cl.[7] .......................... G01N 33/574; C07K 7/00
(52) U.S. Cl. ........................ 435/7.23; 435/7.1; 435/7.2; 435/7.21; 435/4; 530/317; 530/328; 530/300
(58) Field of Search ................................ 435/7.23, 7.1, 435/7.2, 7.21, 4, 6; 530/317, 328, 300

(56) References Cited

U.S. PATENT DOCUMENTS

| | | |
|---|---|---|
| 5,510,240 A | 4/1996 | Lam et al. |
| 5,635,598 A | 6/1997 | Lebl et al. |
| 5,650,489 A | 7/1997 | Lam et al. |
| 5,651,943 A | 7/1997 | Lam et al. |
| 5,840,485 A | 11/1998 | Lebl et al. |
| 5,858,670 A | 1/1999 | Lam et al. |
| 5,888,497 A | 3/1999 | Jain et al. |
| 6,242,211 B1 | 6/2001 | Peterson et al. |
| 2001/0005578 A1 | 6/2001 | Prusiner |

FOREIGN PATENT DOCUMENTS

WO    WO 9827231    12/1997

OTHER PUBLICATIONS

Journal of the American Chemical Soceity (2002), 124(26), 7678–80, Liu et al.*

Liu, Gang, Yemei Fan, James R. Carlson, Zhan–Gong Zhao, and Kit S. Lam. "Solution–Phase Synthesis of a 1,5–Di–alkylamino–2,4–dinitrobenzene Library and the Identification of Novel Antibacterial Compounds from This Library." *J. Comb. Chem* 2, No. 5 (Aug. 3, 2000): 467–474.

Lam, Kit S. "Application of combinatorial library methods in cancer research and drug discovery." *Anti–Cancer Drug Design* 12 (1997): 145–167.

Cabilly, S., ed. *Methods in Molecular Biology*, vol. 87: *Combinatorial Peptide Library Protocols*, chaps. 1 and 2. Totowa, New Jersey: Humana Press, Inc.

Lebl, Michal, Viktor Krchňák, Nikolai F. Sepetov, Bruce Seligmann, Peter Strop, Stephen Felder, and Kit S. Lam. "One–Bead–One–Structure Combinatorial Libraries." *Biopolymers (Peptide Science)* 37 (1995): 177–198.

Liu, Gang, and Kit S. Lam. One–bead one–compound combinatorial library method. In *Combinatorial Chemistry—A Practial Approach*. Edited by Hicham Fenniri. Oxford University Press.

Lam, Kit S., Sydney E. Salmon, Evan M. Hersch, Victor J. Hruby, Wieslaw M. Kazmierski, and Richard J. Kanpp. "A new type of synthetic peptide library for identifying ligand–binding activity." *Nature* 354 (Nov. 7, 1991): 82–84.

Lam, Kit. S. and Michal Lebl. "Selectide Technology: Bead–Binding Screening." *Methods: A Companion to Methods in Enzymology* 6 (1994): 372–380.

Lam, Kit S., Zhan–Gong Zhao, Shelly Wade, Viktor Krchňák, and Michal Lebl. "Identification of Small Peptides That Interact Specifically With a Small Organic Dye." *Drug Development Research* 33 (1994): 157–160.

Wu, Jinzi, Qingyan N. Ma, and Kit S. Lam. "Identifying Substrate Motifs of Protein Kinases by a Random Library Approach." *Biochemistry* 33 (1994): 14825–14833.

Smith, M. H., A. A. Nuara, J. G. Egen, D. B. Sirjani, K. S. Lam, and W. J. Grimes. "Baculoviral expressed HLA class I heavy chains used to screen a synthetic peptide library for Allele–Specific peptide binding motifs." *Molecular Immunology* 35 (1998): 1033–1043.

Pennington, Michael E., Kit S. Lam, and Anne E. Cress. "The use of a combinatorial library method to isolate human tumor cell adhesion peptides." *Moleular Diversity* 2 (1996): 19–28.

Lam, Kit S., Michal Lebl, and Viktor Krchňák. "The 'One–Bead–One–Compound' Combinatorial Library Method." *Chem Rev* 97 (1997): 411–448.

Lam, Kit S. Synthetic peptide and nonpeptide libraries. *Encyclopedia of Molecular Biology and Molecular Medicine* 5 (1996): 516–524.

Lam, Kit S., Thomas Sroka, Man–Ling Chen, Yu Zhao, Qiang Lou, Jinzi Wu. Zhan–Gong Zhao. Appliation of "one–Bead One–Compound" Combinatorial Library Methods in Signal Transdution Research. *Life Sciences* 62, nos. 17/18 (1998): 1577–1583.

(List continued on next page.)

Primary Examiner—T. D. Wessendorf
(74) Attorney, Agent, or Firm—Audrey A. Millemann

(57) ABSTRACT

The invention includes a cell-growth-on-bead assay for screening a one-bead-one-compound combinatorial bead library to identify synthetic ligands for cell attachment and growth or proliferation of epithelial cells. Cells are incubated with a compound bead library for 24 to 72-hours, allowing them to attach and grow on the beads. Those beads with cells growing are removed, and the ligand on the bead is identified. Also provided are ligands specific for epithelial cancer cells. The invention also includes a method of capturing epithelial cells from body fluids. In this method, beads are prepared with a known ligand specific for a particular type of cell and incubated for 24 to 72 hours with a sample of the body fluid being tested. Those cells attached to the beads are removed and identified.

8 Claims, 4 Drawing Sheets

OTHER PUBLICATIONS

Lam, Kit S., Douglas Lake, Sydney E. Salmon, John Smith, Man–Ling Chen, Shelly Wade, Farid Abdul–Latif, Richard J. Knapp, Zuzana Leblova, Ronald D. Ferguson, Viktor Krchnak, Nikolai F. Sepetov, Michal Lebl. A One–Bead One–Peptide Combinatorial Library Method for B–Cell Epitope Mapping. *Methods: A Companion to Methods in Enzymology* 9 (1996): 482–493.

Park, Steven, Renil Manat, Brian Vikstorm, Nail Amro, and Kit S. Lam. "Identifiation of Peptide Ligands for $\alpha 4\beta 1$ Integrin Receptor as Potential Targeting Agents for Non–Hodgkin's Lymphoma." *Peptides: The Wave of the Future.* $2^{nd}$ International Peptide Symposium in conjunction with the $17^{th}$ American Peptide Symposium. Jun. 9–14, 2001, San Diego, CA.

Clark, Peter. 1998. "Micropatterning cell adhesiveness" in *Immobilized Biomolecules in Analysis—A Practial Approach.* Edited by Tony Cass and Frances S. Ligler, Oxford University Press.

DeRoock, Ian B., Michael E. Pennington, Thomas C. Sroka, Kit S. Lam, G. Tim Bowden, Elisabeth L. Bair, and Anne E. Cress. "Synthetic Peptides Inhibit Adhesion of Human Tumor Cells to Extracellular Matrix Proteins." *Cancer Research* 61 (Apr. 15, 2001) 3308–3313.

Lau, Derick H., Linlang Guo, Ruiwu Liu, Aimin Song, Chunkui Shao, and Kit S. Lam. "Identifying peptide ligands for cell surface receptors using cell–growth–on–bead assay and one–bead one–compound combinatorial library." *Biotechnology Letters* 24 (2002) 497–500.

Mařík, Jan, Derik H. Lau, Aimin Song, Xiaobing Wang, Ruiwu Liu, Kit S. Lam. "Magnetization of Large Polystyrene Peptide Beads for Capturing and Expanding Cancer Cells." *Elsevier Science* (Feb. 7, 2003).

Aina, Olulanu H., Thomas C. Sroka, Man–Ling Chen, and Kit S. Lam. "Therapeutic Cancer Targeting Peptides." *Published online Oct. 7, 2002 in Wiley Interscience* (www.interscience.wiley.com).

Liu, Ruiwu, Jan Mařík, and Kit S. Lam. "A Novel Peptide–Based Enoding System for 'One–Bead One–ompound' Peptidomimetic and Small Molecule Combinatorial Libraries." *J. Am. Chem Soc.* 124 (2002) 7678–7680.

Cardareli, Pina M., et al. "The Collagen receptor alpha–2–beta–1, from MG–63 and HT1080 cells, interacts with a cyclic RGD peptide." *Journal of Biologial Chemistry* 267 (1992) 32: 23159–23164.

Durcova, G., et al. "Immunomagnetic Isolation of Mouse Embryonic Stem Cells form Heterogeneous Cell Population." *Theriogenology* 47 (1997) 1: 242.

Krueger, W., et al. "Purging in Der Knochenmark– und Stammzell Transplantation1 Purging in Bone Marrow and Stem Cell Transplantation." *Laboratoriumsmedizien, Kirchheim, De* 20 (1996) 4: 210–220.

Yang Yi, et al. "LPAM–1 (integrin alpha4beta7)–ligand binding: Overlapping binding sites recognizing VCAM–1, MAdCAM–1 and CS–1 are blocked by fibrinogen, a fibronectin–like polymer and RGD–like cyclic peptides." *European Journal of Immunology* 28 (Mar. 1998) 3: 995–1004.

European Patent Application, pub. No. EP 0 332 912 A2 (Jolla Cancer Res Found) Sep. 20, 1989 (published Sep. 20, 1989), "Inhibition of cell migration with synthetic peptides".

* cited by examiner

METHOD FOR SCREENING COMBINATORIAL BEAD LIBRARY, CAPTURING CELLS FROM BODY FLUIDS, AND LIGANDS FOR CANCER CELLS

BACKGROUND OF THE INVENTION

1. Field of the Invention

The invention relates to screening methods for one-bead-one-compound combinatorial libraries and includes a screening assay that uses live cells to identify synthetic ligands that promote attachment and growth or proliferation of epithelial cells. Also included are ligands specific for epithelial cancer cells. The invention also relates to methods for isolating and capturing epithelial cells, including benign (non-cancerous) and malignant (cancerous) cells, from body fluids.

2. Description of Related Art

One-bead-one-compound combinatorial bead libraries (see Lam, Kit S. et al. "A new type of synthetic peptide library for identifying ligand-binding activity." Nature 354 (1991): 82–84), such as one-bead-one-compound peptide libraries, are being used to study cell adhesion properties of cancer cells. Using random peptide bead libraries and suspended cancer cells, peptide ligands that promote cell attachment have been identified for lymphoma (Park, Steven, Renil Manat, Brian Vikstrom, Nail Amro, and Kit S. Lam. "Identification of peptide ligands for α4 β1 integrin receptor as potential targeting agents for non-Hodgkin's lymphoma," abstract in Peptides: The Wave of the Future, 2nd International Peptide Symposium in conjunction with the 17$^{th}$ American Peptide Symposium, San Diego, Calif. (Jun. 9–14, 2001)) and prostate cancer cell lines (Pennington, Michael E., Kit S. Lam and Anne E. Cress. "The use of a combinatorial library method to isolate human tumor cell adhesion peptides." Molecular Diversity 2 (1996): 19–28; DeRoock, Ian B., Michael E. Pennington, Thomas C. Sroka, Kit S. Lam, G. Tim Bowden, Elisabeth L. Bair, and Anne E. Cress. "Synthetic Peptides Inhibit Adhesion of Human Tumor Cells to Extracellular Matrix Proteins." Cancer Research 61 (Apr. 15, 2001): 3308–13).

In the existing methods, live cells in suspension are incubated for about one to four hours with a bead library, and the library is then screened for beads with peptide ligands that promote cell attachment. This is done by visual selection—the beads are examined under a dissecting microscope and those beads with attached cells are removed using a micropipet. Further steps are then performed to confirm that the removed beads are in fact capable of binding the particular type of cells tested. Then, the peptides on those beads are sequenced. (See Pennington et al., "Use of a combinatorial library method," 19–28.)

In another existing method of testing live cells for peptide ligands that affect cell growth on culture plates, a bead library is prepared having selectively cleavable peptides such that a proportion of the peptide on each bead is attached to the bead by a cleavable linker. When the library is treated with a cleaving agent, enough of the peptides are released from the beads to cause the biological effect, and the rest of the peptides remain bound to the beads to allow for later sequencing. Suspended cells are incubated in tissue culture wells with a few beads and with peptides released from the beads. The effect of the released peptides on the cells (inhibition or stimulation of cell growth) is determined, and the corresponding beads are removed. The sequences of the attached peptides are then determined. (See U.S. Pat. No. 5,510,240, issued Apr. 23, 1996 to Lam, Kit S. et al.)

The existing methods, however, are not satisfactory in certain cases. The methods are difficult to use with epithelial cells, which include the majority of solid cancer cell cultures, such as lung cancer cells, that exist as adherent cultures rather than as suspended cells. With incubation periods of only a few hours, these cells are often only weakly attached to the beads and may easily fall off, rendering the screening method less accurate because some beads with attached cells are missed. Also, the existing methods may not detect cell surface receptors that may be altered by trypsin and/or EDTA. Trypsinization is commonly used to separate tissues or cell cultures into a single-cell suspension for testing with a combinatorial library. The treatment with trypsin may eliminate some, or alter the conformation of, cell surface receptors. In addition, the existing methods do not select for peptide ligands that promote cell growth or proliferation, but, rather, for ligands involved in cell attachment, particularly short-term attachment.

Thus, there is a need for a screening assay that is specific and sensitive, works well with epithelial cells, can be used to detect cell surface receptors susceptible to trypsin, and selects for ligands that promote not only cell attachment, but also cell growth or proliferation.

There is also a need for an efficient method of isolating and capturing epithelial cells, including benign and malignant cells, from body fluids, such as blood, urine, pleural effusion, pericardial effusion, ascite, and cerebrospinal fluid. In particular, there is a need for a method of isolating and capturing cancer cells to assist in diagnosis.

SUMMARY OF THE INVENTION

The present invention is directed to a method for screening a combinatorial bead library for ligands that promote the attachment and growth or proliferation of epithelial cells. The method satisfies the need for an assay that is specific and sensitive, that can be used to detect cell surface receptors susceptible to trypsin, and that can identify ligands that promote cell growth and proliferation. The method comprises introducing a suspension of live cells to a combinatorial library of small molecules, peptides, or other types of molecules, incubating the cells with the library for about 24 to 72 hours, identifying a solid phase support of the library with cells growing on the support, isolating the solid phase support, and determining the chemical structure of the compound attached to that solid phase support.

The invention also includes ligands specific for cell attachment and growth or proliferation of epithelial cancer cells, having the chemical structure of cXGXGXXc, in which "c" is D-cysteine; "X" is any L-, D-, unnatural, or modified amino acid; and "G" is glycine.

The present invention is also directed to a method for isolating and capturing cells from body fluids and satisfies the need for an efficient method of isolating and capturing epithelial cells from body fluids. The method comprises introducing a sample of body fluid to a multiplicity of beads with one or more known ligands specific for one or more particular types of cell, incubating the body fluid with the beads for about 24 to 72 hours, identifying a bead with cells growing on the bead, isolating the bead, and recovering the cells growing on the bead.

BRIEF DESCRIPTION OF THE DRAWINGS

FIG. 1 is a diagram depicting the steps of the cell-growth-on-bead assay.

FIG. 2 is a diagram depicting the steps of the method for isolating and capturing epithelial cells from body fluids.

DETAILED DESCRIPTION OF THE PREFERRED EMBODIMENTS

One embodiment of the invention includes a method, referred to as the cell-growth-on-bead assay, for screening a one-bead-one-compound combinatorial bead library for ligands that promote cell attachment and growth or proliferation. Ligands that promote cell attachment and growth or proliferation of cancer cells are also described. Another embodiment of the invention includes a method for isolating and capturing epithelial cells, such as benign or malignant cells, from body fluids. This method can be used to aid in the diagnosis of cancer.

Cell-Growth-on-Bead Assay

The cell-growth-on-bead assay of the first embodiment includes the following steps, as shown in FIG. 1. A one-bead-one-compound combinatorial library is prepared. The library is preferably synthesized using the "split synthesis" approach described in Lam et al., "A new type of synthetic peptide library," 82–84. The compounds of the library may be small molecules, peptides, or other types of molecules. An example of a suitable library is a peptide library containing cXXXXXXc peptides, where "c" is D-cysteine which provides intramolecular cyclization by disulfide bonding, and "X" is any L, D, unnatural, or modified amino acid. A suitable solid phase support, such as beads or discs made of polystyrene, agarose, acrylamide, glass, plastic, or paramagnetic substances, is used. Polystyrene beads have been found satisfactory. A standard synthetic solid phase peptide synthesis method, such as fluorenylmethyoxycarbonyl (Fmoc) chemistry or t-butyloxycarbonyl (Boc) chemistry, is used. For purposes of illustration, the combinatorial library referred to below is a peptide bead library, although it is understood that this is only one example of a library that can be used in this embodiment and that other libraries will also work.

Figure 1A:
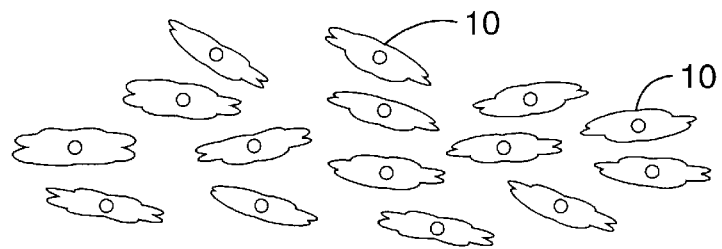
FIG. 1A shows attached epithelial cells.

A suspension of live mammalian cells is prepared according to methods known to those skilled in the art. The cells are preferably epithelial cells and may be cancerous or non-cancerous. Human cancer cells from a cell line or derived from biopsy specimens or body fluid of cancer patients may be used. FIG. 1A shows attached epithelial cells 10.

Figure 1B:
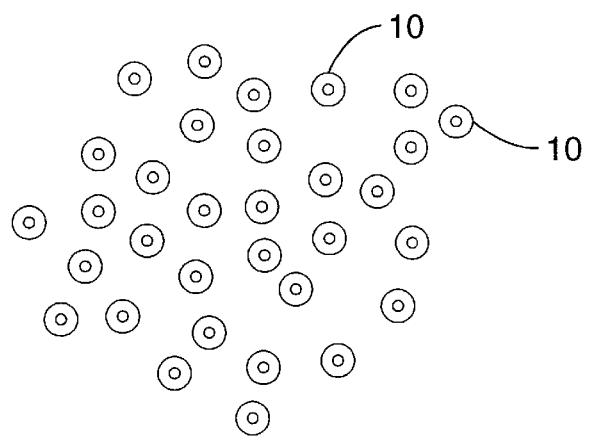
FIG. 1B shows the detached epithelial cells of FIG. 1A in suspension.

FIG. 1B shows the same cells 10 in suspension.

Figure 1C:
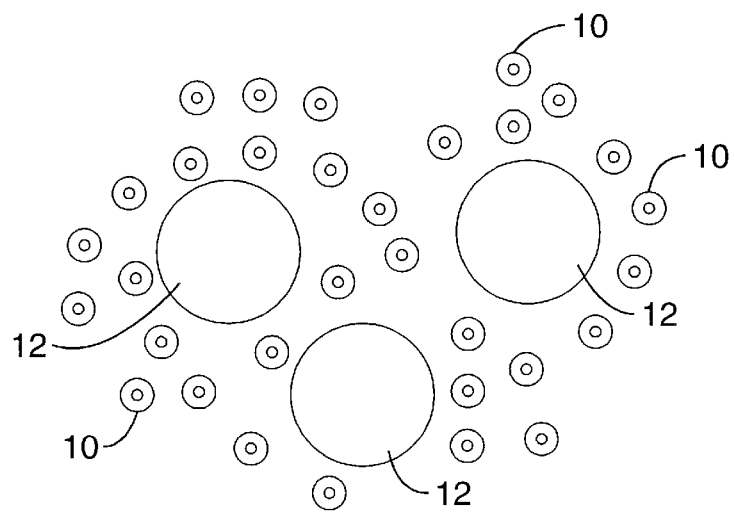
FIG. 1C shows the epithelial cells being mixed with the beads of the bead library.

Suspended live cells 10 are mixed with the peptide library in culture medium, as shown in FIG. 1C, and distributed into culture plates. The ratio of cells to peptide beads is preferably about 10:1, but can range from about 1:1 to 100:1. The suspension of cells 10 and beads 12 is mixed gently for sufficient time to assure contact of beads 12 with suspended cells 10. The culture plates are incubated in a tissue culture incubator at about 4° C. to about 37° C., preferably 37° C., for a period of about 24 to about 72 hours. The suspension of cells 10 and beads 12 may be kept still or mixed, either continuously or intermittently, during the incubation period.

Figure 1D:
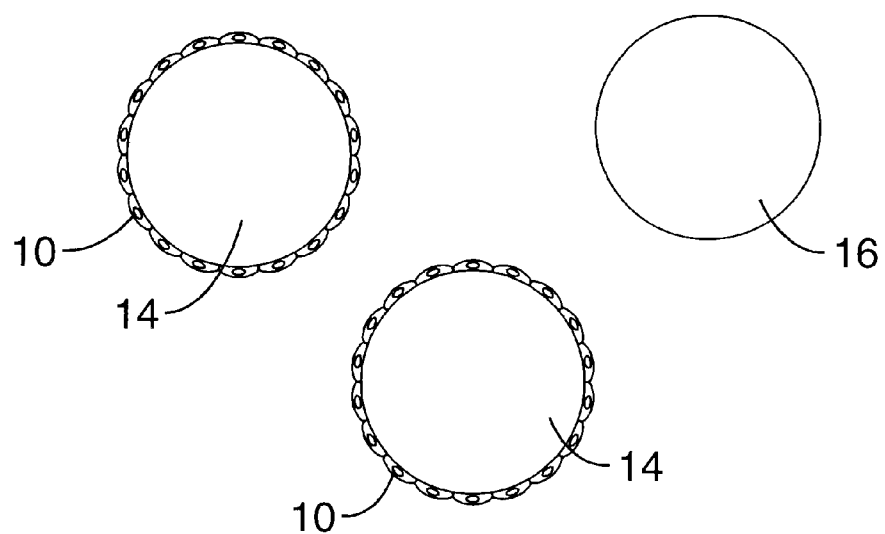
FIG. 1D shows a top view of three beads, in which two beads have a monolayer of cells growing on the bead.
Figure 1E:
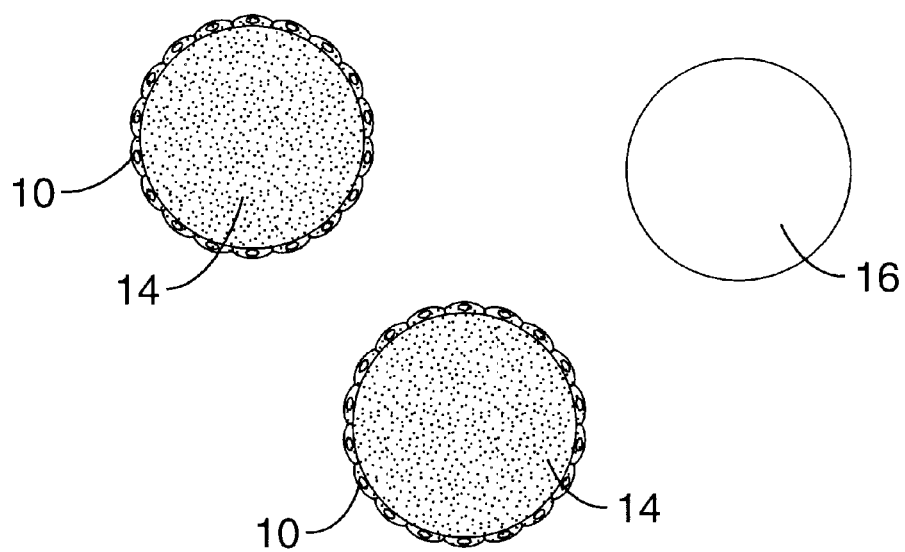
FIG. 1E shows a top view of the three beads of FIG. 1D, after staining, in which the two beads with a monolayer of cells growing on the bead are stained, and the one bead without any cells is not stained.

After the incubation period, beads 12 are observed under a dissecting microscope. The presence of an increased number of cells 10 or beads 14 covered with a monolayer of cells, as shown in FIG. 1D, evidences cell growth or proliferation. These beads 14 (referred to as "positive" beads) are removed from the culture plates. A tetrazolium dye that stains live, but not dead, cells can be used to facilitate the identification and removal of the positive beads. If a dye is used, all of the beads are removed after the incubation period and resuspended in fresh medium in new culture plates. The dye is added. The plates are then incubated in a tissue culture incubator at 25° C. to 37° C. for about one to four hours. Live cells 10 convert the dye to a colored metabolite, which results in beads 14 with attached cells appearing colored, allowing them to be easily distinguished from beads 16 without attached cells, which appear colorless, as shown in FIG. 1E. Other dyes that stain live cells can also be used.

After positive beads 14 are removed from the plates, attached cells 10 are separated from the beads. This can be done with the addition of a chaotrophic agent, such as 8 M guanidine hydrochloride, or a protease, such as trypsin.

The amino acid sequence of the ligand on each isolated positive bead 14 is then determined. This is preferably done with an automated protein sequencer, such as the Procise 494 (Applied Biosystems, Foster City, Calif). Alternatively, the peptide can be released via a cleavable linker and the amino acid sequence determined by mass spectroscopy. If the ligand on the bead consists of a small molecule, mass spectroscopy, and/or encoding strategies can be used.

Using the cell-growth-on-bead assay of the first embodiment, ligands that promote cell attachment and growth or proliferation have been identified. By structure/activity relationship studies, ligands identified for epithelial cancer cells, such as those of lung cancer, have the general structure of cXGXGXXc, where "c" is D-cysteine; "X" is any L, D, unnatural, or modified amino acid; and "G" is glycine.

Method of Isolating and Capturing Cells from Body Fluids

The second embodiment of the invention is a method to isolate and capture benign or malignant epithelial cells from mammalian body fluids as shown in FIG. 2. The method can be used to capture cancer cells from body fluids, such as blood, urine, pleural effusion, pericardial effusion, ascite, and cerebrospinal fluid.

Figure 2A:
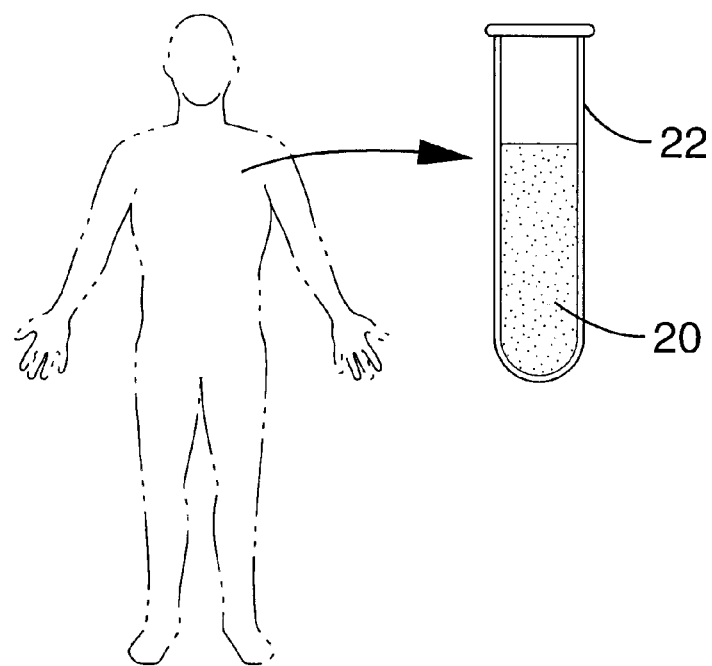
FIG. 2A shows a centrifuge tube containing a sample of body fluid, containing cells, which has been removed from the human body.
Figure 2B:
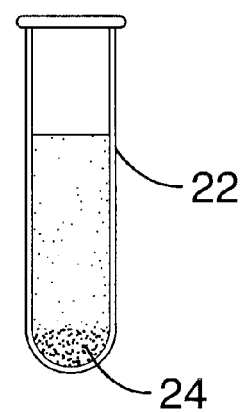
FIG. 2B shows the centrifuge tube containing the body fluid, in which the cells have been allowed to sediment.

As shown in FIG. 2A, a sample of fluid 20 is removed from the body and placed in centrifuge tube 22 for about 10 minutes to allow cells 24 to settle to the bottom, as shown in FIG. 2B. A sample of the sediment containing cells 24 is then resuspended in culture medium. About 0.1 to 0.5 ml of sediment in about 2 ml of culture medium works well.

A suitable solid phase support, such as beads or discs made of polystyrene, agarose, acrylamide, glass, plastic, or paramagnetic substances, is used. Polystyrene beads have been found to be satisfactory. For purposes of illustration, beads are used as the solid phase support. Approximately 5,000 to 10,000 beads containing one or more known ligands specific for one or more particular cell types are sterilized with ethanol. The ligands may consist of small molecules, peptides, or other molecules. Generally, one ligand is used; however, more than one ligand may also be used.

Figure 2C:
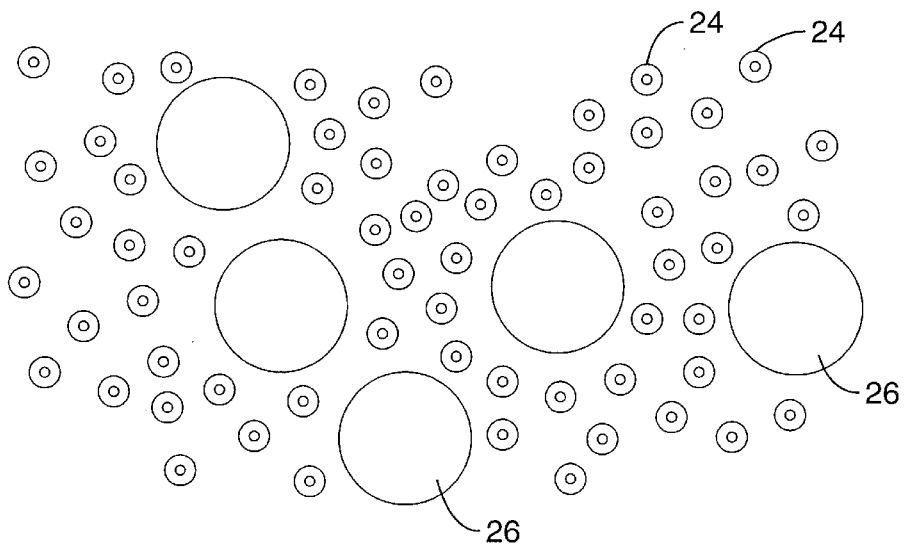
FIG. 2C shows the cells being mixed with beads.
Figure 2D:
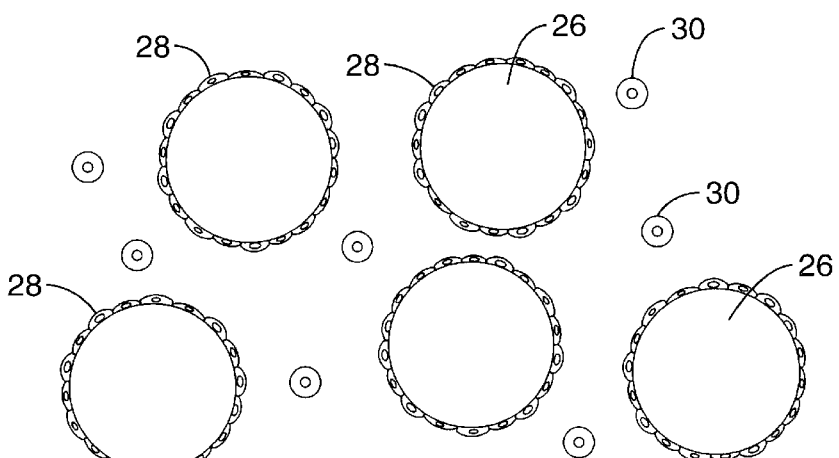
FIG. 2D shows a top view of the beads and the cells, in which some cells are attached and growing on the beads, and some cells remain unattached.

The cell suspension and sterile beads 26 are mixed gently in a cell culture dish for a few minutes to assure contact of beads 26 with suspended cells 24, as shown in FIG. 2C. The mixture is incubated in a tissue culture incubator under 5% carbon dioxide at about 4° C. to about 37° C., preferably 37° C. The dish is observed under a microscope daily for a period of about 24 to about 72 hours to check for cell attachment and growth, as shown in FIG. 2D. The medium may be changed if necessary. Typically, a culture can be maintained for up to about four weeks depending on the rate of cell proliferation on the beads. Cells 28 attached to beads 26 are recovered when the number of cells is sufficient for counting, morphologic examination, molecular analysis, and further culturing.

Figure 2E:
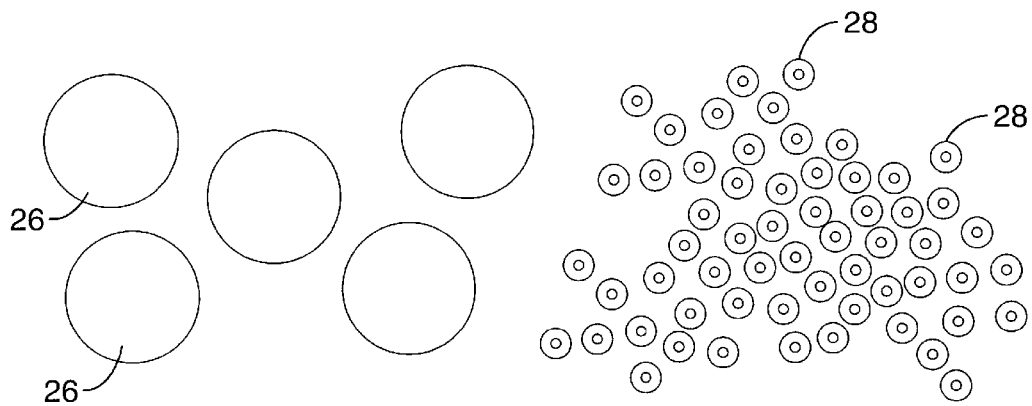
FIG. 2E shows the beads and the cells after the cells have been removed from the beads.

The medium is pipetted off the culture dish, and beads 26 with attached cells 28 are rinsed with fresh medium to remove unattached cells 30, such as red blood cells, and other cell debris. Beads 26 with attached cells 28 are transferred to a fresh dish. Attached cells 28 are removed from beads 26 with trypsin and/or EDTA, as shown in FIG. 2E. Isolated cells 28 are transferred to a centrifuge tube containing fresh culture medium and concentrated by centrifugation at 500×g. The supernatant is removed, and the cells are spread on a glass slide by direct smearing or by cytospin. Cells on glass slides can be preserved in fixatives such as 95% alcohol and then stained with Giemsa or Papanicolou stain for subsequent morphologic examination.

The concentrated cells can also be fixed in 10% formalin or 4% paraformaldehyde and embedded in paraffin. The cell block can be sectioned into 5μ slices and placed on glass slides for morphologic staining and/or immunohistochemical staining to identify special antigens, for example, carcinoembryonic antigen (CEA) and estrogen receptor (ER), if necessary to aid in diagnosis of cancer. In addition, the cells recovered can be analyzed with other cellular or molecular techniques such as laser scanning cytometry, Western blotting, and microarray.

The cells recovered from the beads may also be cultured for expansion of cell number or for long-term maintenance. After having been separated from the beads, cells are pipetted into a 15 ml centrifuge tube. The cell pellet is resuspended in an appropriate amount of medium in a culture dish or flask. The cell culture is kept in a tissue culture incubator under 5% carbon dioxide at 37° C. Cells harvested from the culture can be stored long-term in 90% serum and 10% DMSO under liquid nitrogen.

Example of Cell-Growth-on-Bead Assay

A one-bead-one-peptide combinatorial library, containing random cXXXXXXc peptides, was prepared using the "split synthesis" method of Lam et al., "A new type of synthetic peptide library," 82–84. The random peptide library contained $19^6=4.7\times10^7$ possible permutations of the formula cXXXXXXc, where "c" is D-cysteine, and "X" is one of 19 natural L-amino acids.

TentaGel polystyrene beads, with a diameter of 80 μm and with grafted polyethylene glycol of 0.25 mmol/g, were used as a solid phase support (Rapp Polymere, Germany). A synthetic solid phase method using fluorenylmethyoxycarbonyl (Fmoc) chemistry was adapted for synthesizing the peptide bead library.

The non-small-cell lung cancer cell line, A549 (American Type Culture Collection, Manassas, Va.), was used. The cell line was maintained in appropriate culture media as recommended by American Type Culture Collection. Cells were grown to confluency in DMEM culture medium supplemented with 10% fetal calf serum. Attached cells were recovered with trypsin/EDTA, washed, and resuspended as single cells in culture medium.

About 150,000 peptide beads were mixed with approximately one million suspended cells in 15 ml of culture medium and distributed into six 3-cm culture plates. The culture plates were agitated gently at about 100 rpm for about 10 minutes. The culture plates were then incubated in a tissue culture incubator at 37° C. for about 24 hours to about 72 hours.

A dissecting microscope was used to examine the beads at about 24, 48, and 72 hours. After about 24 to 72 hours, beads with a monolayer of cells were observed. Out of a library of about 150,000 beads, about 20 to 30 beads typically exhibited cell growth.

At the end of the incubation period, all of the beads were removed and resuspended in fresh medium in a new culture plate. An MTT ([3-(4,5-dimethylthiazol-2-yl)-2,5-diphenyl] tetrazolium bromide) (Sigma, St. Louis, Mo.) dye solution was added to each culture plate to a final concentration of 0.5 mg/ml. The plates were incubated in a tissue culture incubator at 37° C. for about two hours to allow the purple color to develop. Each purple-colored peptide bead was isolated and removed. The attached cells were separated from the beads with 8 M guanidine hydrochloride.

The amino acid sequence of each isolated peptide bead was determined using an automated Procise 494 protein sequencer (Applied Biosystems, Foster City, Calif.). Several consensus peptide sequences were determined, one of which was cNGRGEQc, where "c" is D-cysteine. This peptide was resynthesized on beads, which were then rescreened with the A549 cells using the assay of the invention. Virtually all of the beads with this sequence exhibited cell attachment and growth on their surfaces.

To test the sensitivity of the assay, blank beads and a linear XXXXXX peptide bead library of 150,000 beads were each spiked with 10 positive peptide beads carrying the sequence cNGRGEQc. These libraries were each screened with the A549 cells. The peptide beads with the sequence of cNGRGEQc were isolated with a recovery rate of 90% to 100% in two separate experiments.

To test cell type specificity of beads carrying the peptide ligand cNGRGEQc, cell growth of two other non-small-cell lung cancer cell lines, Calu-1 and H178, was observed on 70% to 90% of the peptide beads. On the other hand, cell growth was observed on only 10% of the peptide beads with the non-malignant bronchoepithelial cell line, HBE-1. Thus, the cNGRGEQc peptide is a ligand specific for promoting cell attachment and growth of malignant cells of the lung.

Through additional secondary library screening and structure/activity relationship studies, other ligands for epithelial cells have been identified, including the following, where "c" is D-cysteine: c-DGChgGAN-c, where Chg is α-cyclohexylglycine; c-NGBpaGQM-c, where Bpa is 4-benzoylphenylalanine; c-NGAcdtGDBpa-c, where Acdt is 4-amino-4-carboxy-1,1-dioxo-tetrahydrothiopyran; c-NGTGDG-c; c-NGQGAG-c; c-NGYGSF-c; and c-NGNleGYG-c, where Nle is norleucine.

Example of Method for Isolating and Capturing Cells from Body Fluid

A sample of human pleural fluid was placed in a centrifuge tube, and the cells were allowed to settle to the bottom of the tube for 10 minutes. A sample of about 0.1 to 0.5 ml of the sediment containing the cells was resuspended in about 2 ml of culture medium.

TentaGel polystyrene beads, with a diameter of 80 µm and with grafted polyethylene glycol of 0.25 mmol/g, were used as a solid phase support (Rapp Polymere, Germany). Approximately 5,000 to 10,000 beads having the ligand cNGRGEQc were prepared. The beads were sterilized with 75% ethanol. The cell suspension and the sterile beads were mixed gently in a 3-cm cell culture dish for five minutes. The dish was incubated in a tissue culture incubator under 5% carbon dioxide at 37° C. The dish was observed daily under a microscope for about 24 to 72 hours to check for cell attachment and/or growth. Cell growth was observed at 24 hours. Cells attached to beads were recovered after 72 hours.

The medium was pipetted off the culture dish, and the beads were rinsed with fresh medium to remove unattached cells, such as red blood cells, and other cell debris. Attached cells were removed from the beads with trypsin/EDTA, transferred to a centrifuge tube with fresh culture medium, and concentrated by centrifugation at 500×g. The supernatant was removed, and the cells were spread on a glass slide by direct smearing or by cytospin. Cells on glass slides were preserved in 95% alcohol and stained with Giemsa or Papanicolou stain. The cells were identified as malignant adenocarcinoma cells which had a large nucleus, prominent nucleoli, and mucin in the cytoplasm.

The invention has been described above with reference to the preferred embodiments. Those skilled in the art may envision other embodiments and variations of the invention that fall within the scope of the claims.

We claim:

1. A method of identifying a peptide ligand that promotes cell attachment and proliferation, comprising:

introducing a suspension of live mammalian cells to a one-bead-one-compound combinatorial peptide library, wherein said library comprises multiple beads with synthetic compounds attached thereto;

incubating said cells with said beads of said library for a period of about 24 to about 72 hours;

identifying a bead having cells growing thereon;

isolating said identified bead; and determining the chemical structure of the compound attached to said identified bead.

2. A method for isolating and capturing epithelial mammalian cells of a particular type from body fluid, comprising:

introducing a sample of body fluid to a multiplicity of beads having a known ligand specific for a particular type of cell;

incubating said body fluid with said beads for a period of about 24 to about 72 hours;

identifying a bead having cells growing thereon;

isolating said bead; and recovering the cells, growing on said isolated bead.

3. The method of claim 2, wherein said incubating is at a temperature of about 37° C.

4. The method of claim 2, wherein said ligand is a peptide specific for a cancer cell.

5. The method of claim 2, wherein said ligand is specific for human epithelial lung cancer cells and has the chemical structure of cXGXGXXc, in which "c" is D-cysteine; "X" is an amino acid selected from the group consisting of L-amino acids, D-amino acids, and unnatural amino acids; and "G" is glycine.

6. The method of claim 5, wherein said ligand has the chemical structure cNGRGEQc, in which "c" is D-cysteine.

7. The method of claim 6, wherein said body fluid is human pleural fluid.

8. A ligand specific for human epithelial lung cancer cells, wherein said ligand has the chemical structure of cXGXGXXc, in which "c" is D-cysteine; "X" is an amino acid selected from the group consisting of L-amino acids, D-amino acids, and unnatural amino acids; and "G" is glycine.

* * * * *